United States Patent
Hoppe et al.

(10) Patent No.: US 7,912,271 B2
(45) Date of Patent: Mar. 22, 2011

(54) METHOD FOR DETERMINING FINAL PROJECTION MATRICES

(75) Inventors: Stefan Hoppe, Amberg (DE); Joachim Hornegger, Effeltrich (DE); Günter Lauritsch, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 852 days.

(21) Appl. No.: 11/903,164

(22) Filed: Sep. 20, 2007

(65) Prior Publication Data

US 2008/0080758 A1 Apr. 3, 2008

(30) Foreign Application Priority Data

Sep. 21, 2006 (DE) .................. 10 2006 044 661

(51) Int. Cl.
G06K 9/00 (2006.01)
A61B 6/03 (2006.01)
(52) U.S. Cl. ........ 382/132; 382/128; 382/130; 382/131; 378/4; 378/210; 378/901; 345/164
(58) Field of Classification Search .................. 382/128, 382/130, 131, 132; 378/4, 210, 901, 205; 345/473, 646
See application file for complete search history.

(56) References Cited

U.S. PATENT DOCUMENTS

| 7,359,477 | B2 * | 4/2008 | Lauritsch et al. | 378/4 |
| 7,559,694 | B2 * | 7/2009 | Gorges et al. | 378/207 |
| 2003/0076327 | A1 * | 4/2003 | Qi | 345/473 |
| 2006/0039537 | A1 * | 2/2006 | Strobel | 378/197 |
| 2006/0182216 | A1 | 8/2006 | Lauritsch et al. | |
| 2007/0172033 | A1 | 7/2007 | Gorges et al. | |

FOREIGN PATENT DOCUMENTS

DE 10 2005 059 301 A1 6/2006

OTHER PUBLICATIONS

Hartley et al., "Multiple View Geometry in Computer Vision", Cambridge University Press, Jun. 2000; Others; 2000.
Fieldcamp et a., "Practical Cone-Beam Algorithm", JOSA A1, 612 (1984), Journal of Optical Society of America, vol. 1, No. 6, Jun. 1984, pp. 612-619; Journal of the Optical Society of America; Magazine; 1984.
Katsevich, "Reconstruction for the Circle-and-Arc Trajectory". Phys Med Biol. May 21, 2005; 50 (10), pp. 2249-2265. Epub Apr. 27, 2005.; Magazine.

(Continued)

Primary Examiner — Wesley Tucker
Assistant Examiner — Nancy Bitar

(57) ABSTRACT

A computer receives a number of groups of projection images of a reference object already known to the computer. Each projection image was captured via a recording arrangement with corresponding positioning of the recording arrangement. The computer uses one projection image for the respective position of the recording arrangement to determine an interim projection matrix, which describes a mapping of the three-dimensional space to a projection image captured with the respective positioning of the recording arrangement. The interim projection matrices relate to coordinate systems that are specifically assigned to each group. The computer uses interim projection matrices of different groups determined for the same position of the recording arrangement to determine locations of the other coordinate systems related to one of the coordinate systems. The computer uses the interim projection matrices and locations of the other coordinate systems to define a final projection matrix, that relates to a uniform coordinate system, for every position of the recording arrangement.

20 Claims, 7 Drawing Sheets

OTHER PUBLICATIONS

Pack et al., "Cone-beam reconstruction using 1D filtering along the projection of M-Lines", Inverse Problems 21, pp. 1105-1120, Print publication: Issue 3 (Jun. 2005), Published Apr. 29, 2005.

Kudo et al., "Fast and stable cone-beam filtered backprojection method for non-planar orbits", Phys. Med. Biol. 43, Apr. 1998, pp. 747-760, Print publication: Issue 4 Magazine.

Wang et al., "A cone-beam reconstruction algorithm for circle-plus-arc data-acquisition geometry", Medical Imaging, IEEE Transactions on Medical Imaging vol. 18, Issue 9, Sep. 1999, pp. 815-824, Magazine.

Xiangyang Tang and Ruola Ning; A cone beam filtered backprojection (CB-FBP) reconstruction algorithm for a circle-plus-two-arc orbit; Medical Physics—Jun. 2001—vol. 28, Issue 6, pp. 1042-1055; Magazine; 2001.

Siemens Medical Solutions; AXIOM Artis dBa, AXIOM Artis dBa DynaCT, "Biplane C-arm System with Flat Detector for Angiography"Data Blatt, A91001-M1400-G940-2 Druckzeichen AX CRM NA 04053.

Norbert Strobel, Benno Heigl, Thomas Brunner, Oliver Schütz, Matthias Mitschke, Karl Wiesent and Thomas Mertelmeier, "Improving 3D Image Quality of X-ray C-Arm Imaging Systems by Using Properly Designed Pose Determination Systems for Calibrating the Projection Geometry", Medical Imaging 2003: Physics of Medical Imaging, Proceedings of SPIE vol. 5030, pp. 943-954.

\* cited by examiner

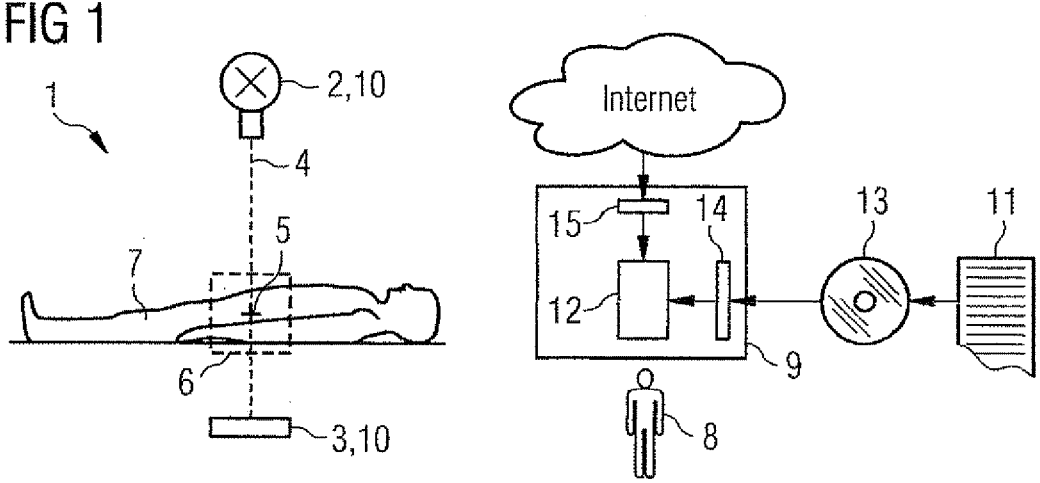
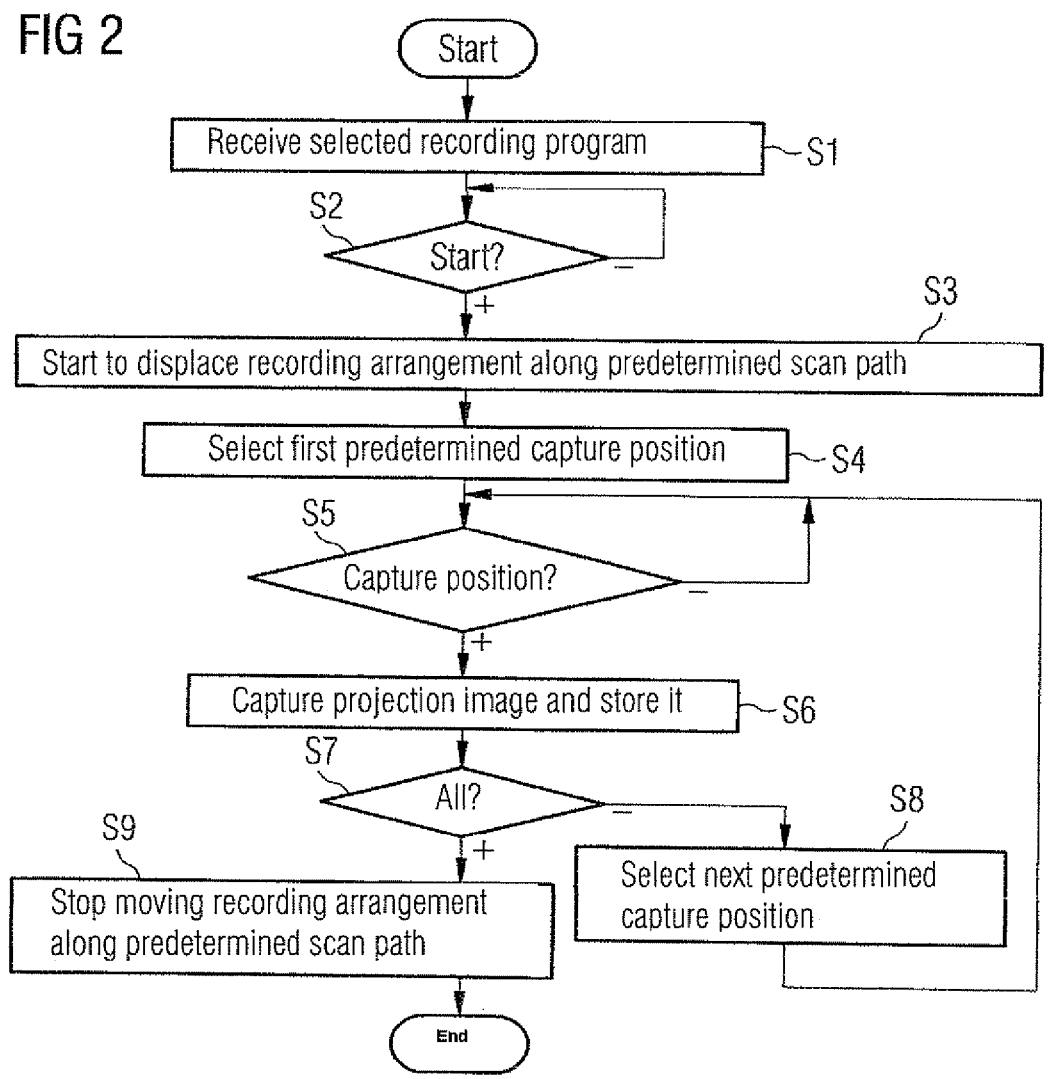

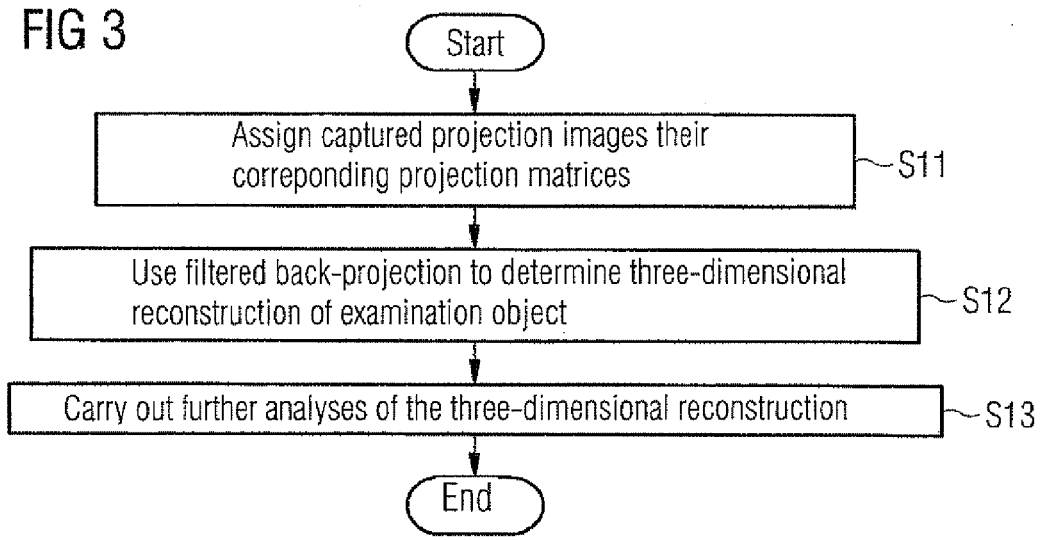
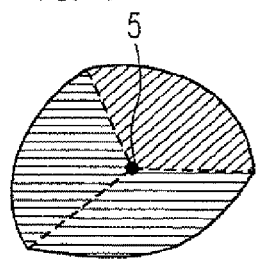
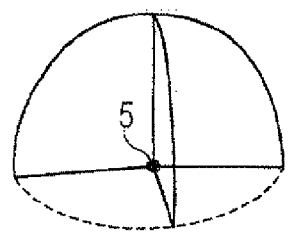
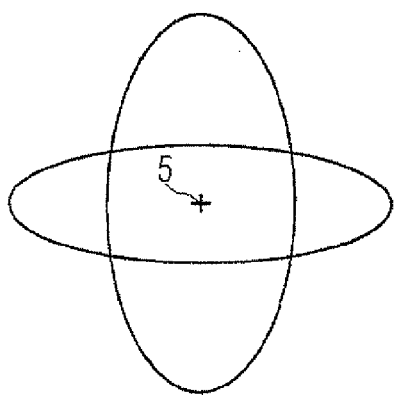
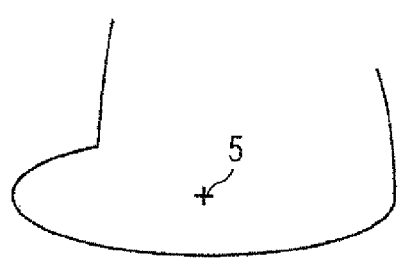

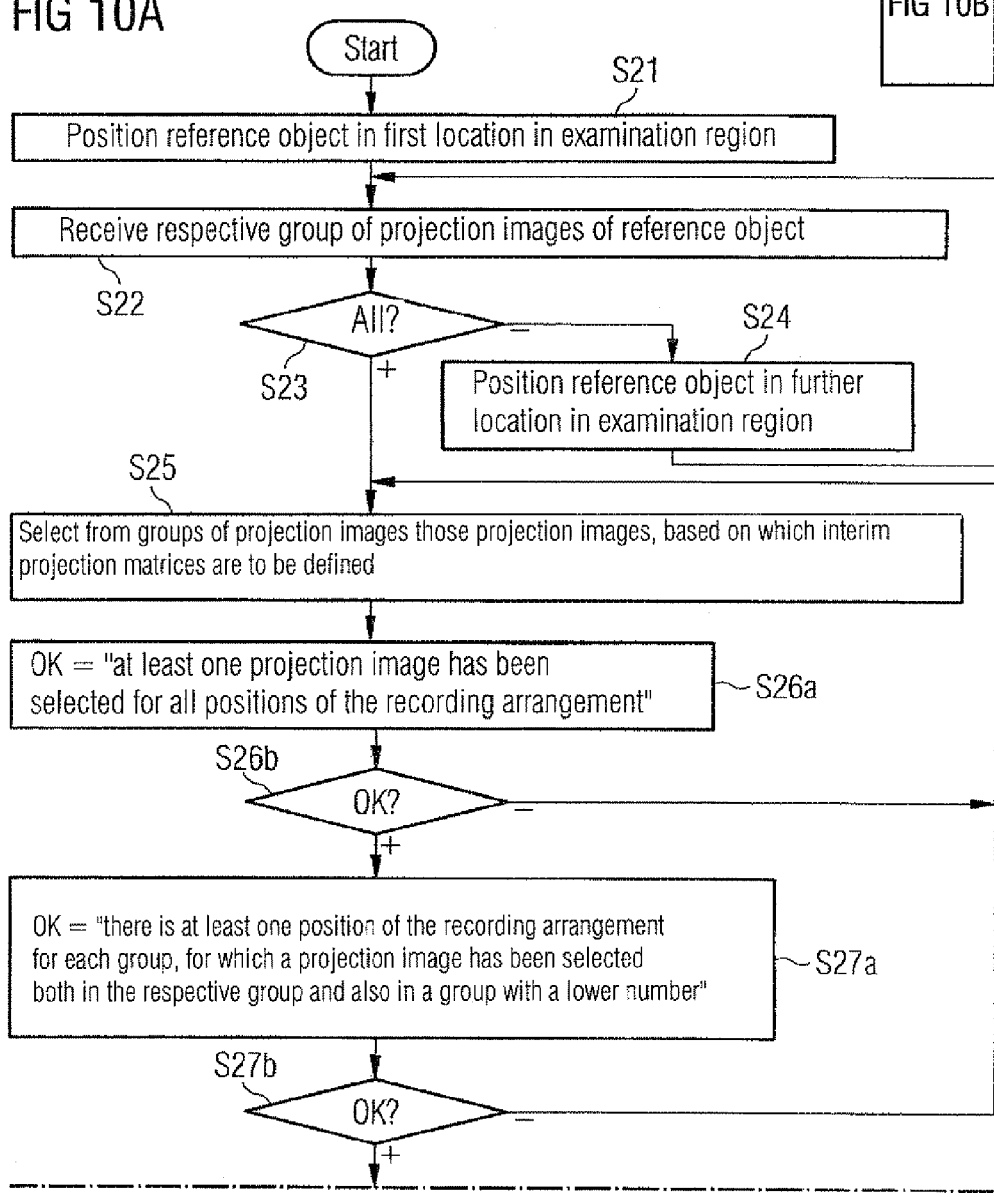

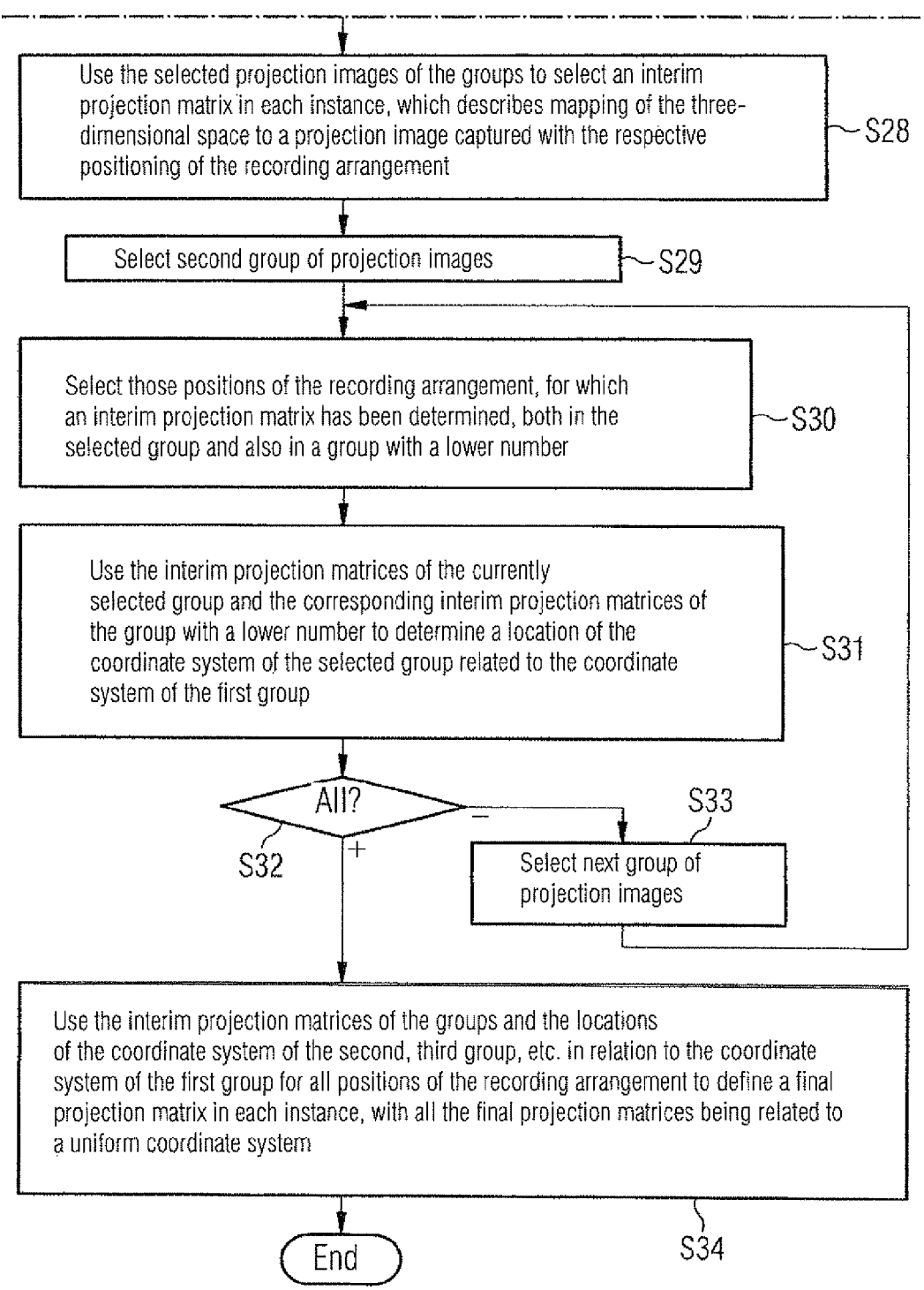

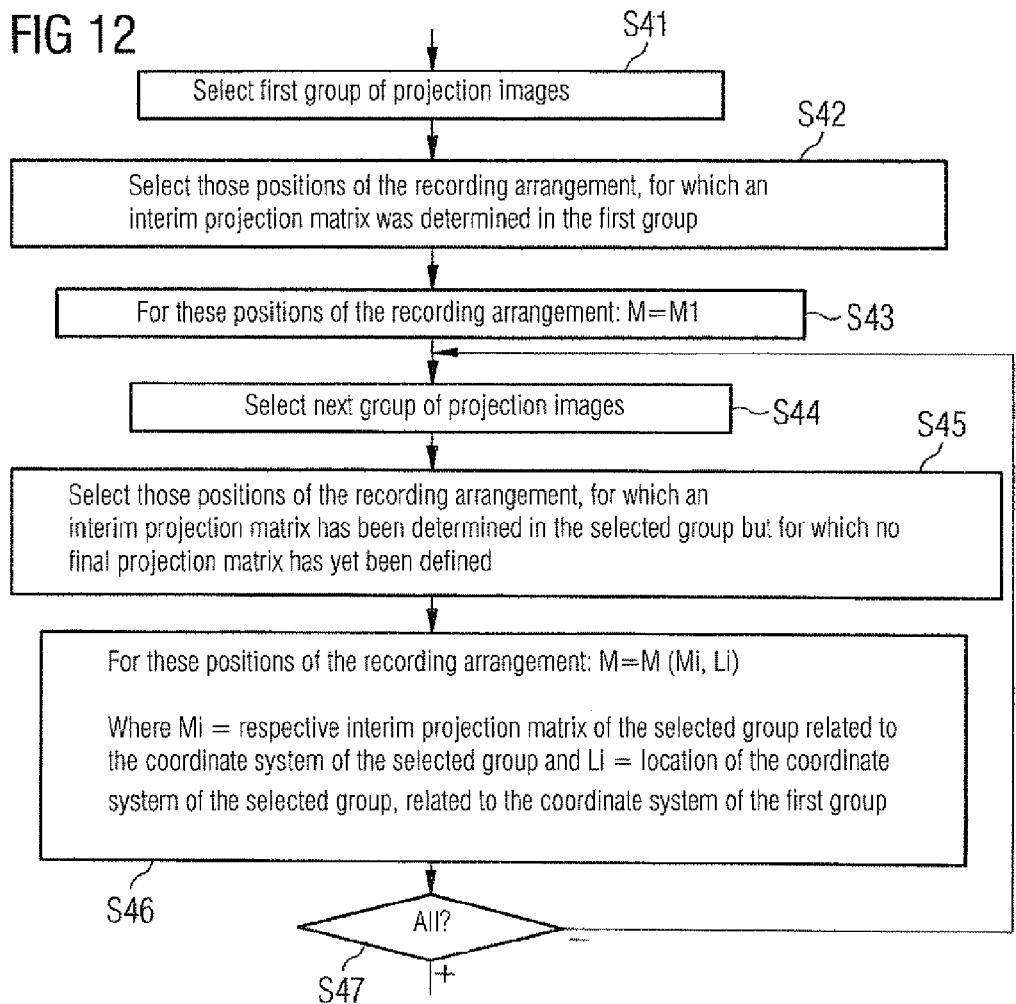
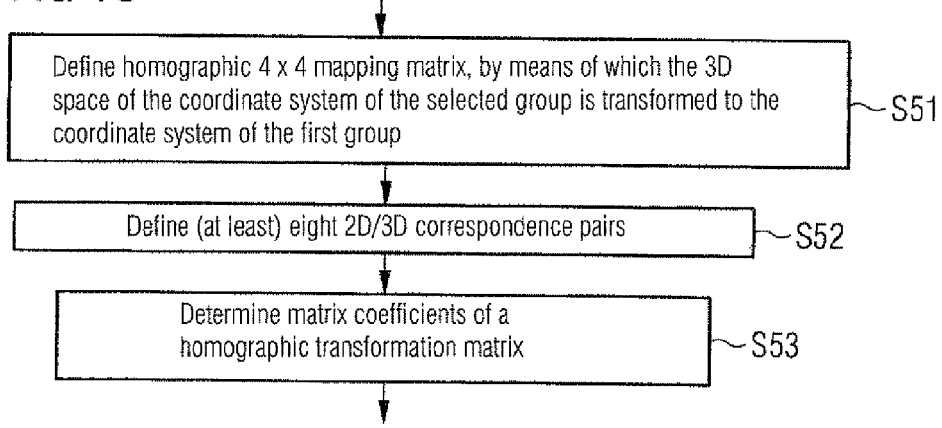

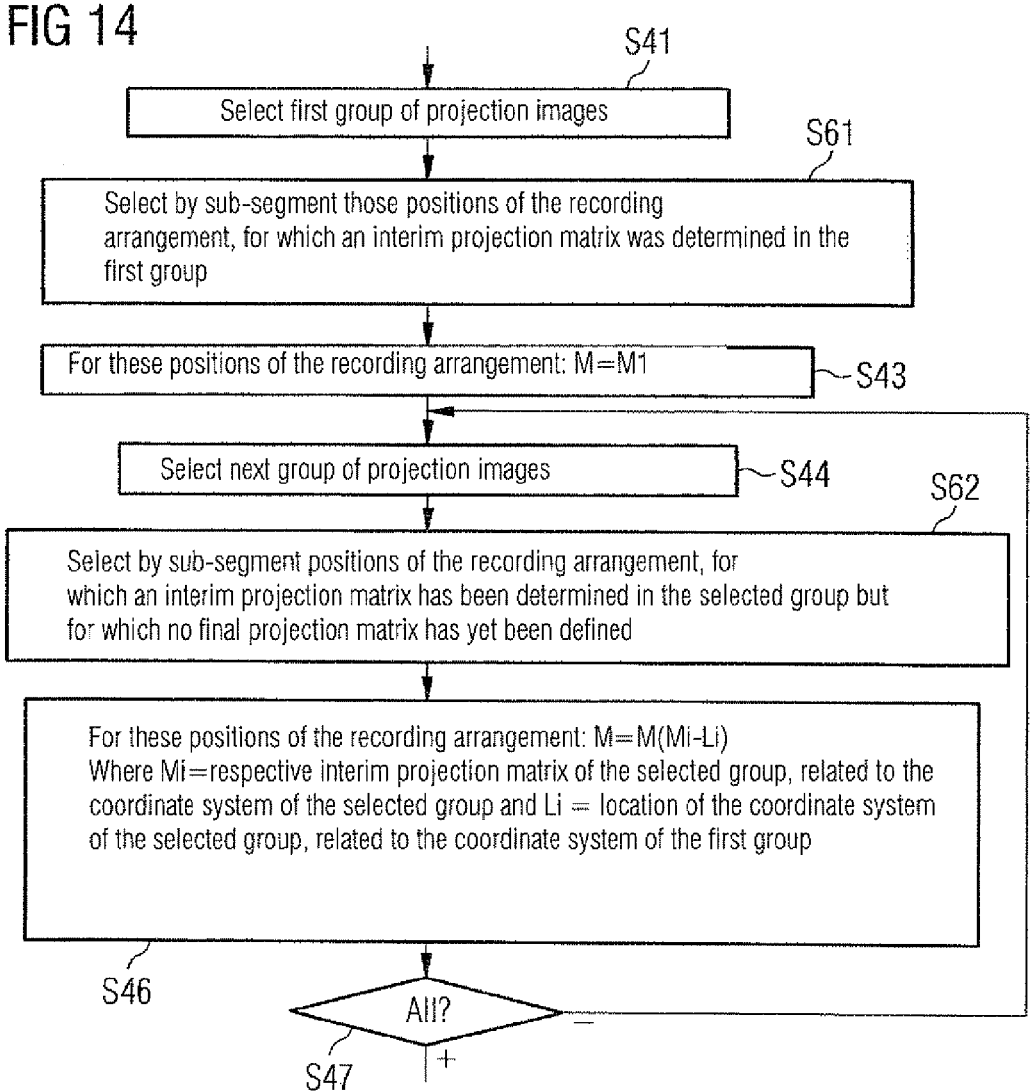

METHOD FOR DETERMINING FINAL PROJECTION MATRICES

CROSS REFERENCE TO RELATED APPLICATIONS

This application claims priority of German Patent Office application No. 10 2006 044 661.5 filed Sep. 21, 2006, which is incorporated by reference herein in its entirety.

FIELD OF INVENTION

The present invention relates to a method for determining final projection matrices. Determination methods of this type are generally known to those skilled in the art.

BACKGROUND OF THE INVENTION

It is known in the prior art that an examination object can be disposed in the examination region of a medical imaging system, for example in the examination region of an x-ray system. A radiation source is moved around the examination object on an essentially planar, essentially circular scan path. A radiation detector is also moved around the examination object on an essentially planar, essentially circular scan path at the same time as the radiation source. The movements of the radiation source and radiation detector are linked in such a manner that the examination object (or the relevant part of the examination object) is constantly located between the radiation source and radiation detector. As the radiation source and radiation detector move, the radiation detector is used to capture two-dimensional projection images of the examination object. What is known as a filtered back-projection algorithm is used to determine a three-dimensional reconstruction of the examination object from the captured two-dimensional projection images. The Feldkamp algorithm in particular is generally known to those skilled in the art and is described for example in the technical paper [1].

For an expedient application of filtered back-projection algorithms the projection matrix of every two-dimensional projection image must be known, this being a matrix, which correctly describes the mapping of the three-dimensional space to the plane, in which the radiation detector is located on receipt of the respective projection image.

It is in theory conceivable to determine the parameters, which define the respective projection matrix, directly from the positioning and orientation of the radiation source and radiation detector and to define the projection matrix based on these parameters. In practice however this procedure proves to be too inaccurate—for example due to mechanical instabilities.

In practice a reference object is disposed in the examination region. Projection images of the reference object are captured from exactly the same positions of the radiation source and radiation detector, from which projection images of examination objects are to be captured later. With a suitable arrangement of the reference object it is possible to define the parameters, which define the projection matrix for the respective projection image, and therefore also the projection matrix itself from each projection image. This procedure is generally known to those skilled in the art and is described in more detail in the technical paper [7] for example.

For each projection image the projection matrices are related to a coordinate system, the location (in other words position and orientation) of which is defined in relation to the reference object. In order to be able to effect a three-dimensional reconstruction, the projection matrices of all the projection images used also have to relate to the same coordinate system. The reference object must therefore not only be disposed in the beam path or in the examination region, it also cannot be moved as the projection images are being captured.

The procedure described above for determining the projection matrices provides good results for standard filtered back-projection algorithms, which assume an essentially circular scan path.

In recent times reconstruction algorithms have become known, which are based on non-circular scan paths. The new types of scan paths consist for example of two circular paths intersecting each other orthogonally or one scan path consisting of a number of circular segments. Tests with simulated data show that these reconstruction algorithms have the potential to improve reconstruction accuracy. See also technical papers [2] to [6].

In principle the method for determining projection matrices described above can also be used for these reconstruction algorithms. In practice the problem however arises that standard reference objects were developed to determine the projection matrices for circular scan paths. Determining the projection matrices for positions of the radiation source and radiation detector, which do not lie on such a circular scan path, is however—depending on the location of the individual case—subject to greater inaccuracies, only possible to a limited degree and with difficulty or impossible.

It is of course possible to determine the projection matrices for the scan path to be traveled in segments, with the reference object being positioned correspondingly for every segment of the scan path. This means that the projected matrices are related to the same coordinate system within each segment of the scan path. It cannot however be ensured that the coordinate systems of different segments correspond. This is however essential when applying the reconstruction algorithms.

It is also conceivable that a reference object can be developed, with which it is possible to determine the projection matrices for all the projection images captured while traveling the respective scan path. However this is associated with a considerable development and financial outlay. Also it is currently not foreseeable whether such attempts will meet with the desired success.

SUMMARY OF INVENTION

The object of the present invention is therefore to create a method for determining final projection matrices, with which the final projection matrices are related to a uniform coordinate system, even though the reference object was not always in the same place when the projection images of the reference object were being captured.

The object is achieved by a determination method, a computer program, a data medium and a computer as claimed.

According to the invention a computer receives a number of groups of projection images of a reference object already known to the computer. Each projection image was captured by means of a recording arrangement with corresponding positioning of the recording arrangement. The computer uses one projection image in each instance to determine an interim projection matrix in each instance for the respective position of the recording arrangement. Each interim projection matrix describes a mapping of the three-dimensional space to a projection image captured with the respective positioning of the recording arrangement. It is related to a coordinate system. A specific coordinate system is assigned to each group of projection images. The computer uses interim projection matrices of different groups determined for the same position of the recording arrangement to determine locations of the other coordinate systems related to one of the coordinate systems. The computer uses the interim projection matrices and locations of the other coordinate systems to define the final projection matrix for every position of the recording arrangement, with the final projection matrices being related to a uniform coordinate system.

The interim and final projection matrices are preferably 3×4 matrices, which define a projective mapping.

The location of the uniform coordinate systems can in principle be selected anywhere. The center point between the origin of the one coordinate system and the origin of one of the other coordinate systems can be selected for example and the orientation of one of the coordinate systems can be adopted. However the computer preferably adopts the location of the one coordinate system as the reference coordinate system. This procedure reduces computation outlay, as many of the interim projection matrices (namely the interim projection matrices related to this coordinate system) can be adopted directly.

In particular the computer can adopt the interim projection matrix for at least one position of the recording arrangement, for which it has determined an interim projection matrix related to the one coordinate system, as the final projection matrix and can determine the final projection matrix for at least one position of the recording arrangement, for which it has determined an interim projection matrix related to another coordinate system, based on the respective interim projection matrix related to the other coordinate system and the location of the other coordinate system.

It is possible for the computer to adopt the respective interim projection matrix as the final projection matrix for any position of the recording arrangement, for which it has determined an interim projection matrix related to the one coordinate system. In this instance the computer can determine the final projection matrix for every position of the recording arrangement for which it has determined an interim projection matrix but this interim projection matrix is not related to the one coordinate system, based on the respective interim projection matrix and the location of the coordinate system, to which the respective interim projection matrix is related.

However the following procedure is preferred: The final projection matrices form a sequence. The sequence has sub-segments. The final projection matrices of each sub-segment correspond to a locally contiguous segment of a scan path, along which the recording arrangement is displaced. The computer determines the final projection matrices based on the interim projection matrices of the same group within each sub-segment. In this process the computer takes account as far as necessary of the location of the coordinate system, to which the respective interim projection matrices are related.

To determine the final projection matrices the computer preferably determines corresponding transformation matrices, on the basis of which the other coordinate systems are transformed to the one coordinate system.

The computer preferably determines a homographic transformation matrix for every other coordinate system, by means of which the three-dimensional space of the respective other coordinate system is transformed to the one coordinate system. The computer uses the respective homographic transformation matrix to transform the interim projection matrices related to the respective other coordinate system to the one coordinate system. The homographic transformation matrices in this instance thus form transformation specifications, based on which the interim projection matrices are transformed to the one coordinate system. This procedure has the advantage that the respective transformation specification can be determined by resolving a linear equation system.

To determine the homographic transformation matrix the computer preferably carries out a singular value decomposition of the equation system, thus determining the matrix coefficients of the homographic transformation matrix. Computation outlay can be further reduced with this procedure. Possible ways and means for determining and resolving the linear equation system are generally known to those skilled in the art and are described for example in the technical publication [8].

In theory the procedure described above is exact. However in practice errors still occur. By resolving the linear equation system, the degree of error relating to the projection images is minimized. This procedure gives better results than when a degree of error relating to the three-dimensional space is optimized.

BRIEF DESCRIPTION OF THE DRAWINGS

Further advantages and details will emerge from the description which follows of an exemplary embodiment in conjunction with the schematic diagrams in the drawings, in which:

FIG. 1 shows a block circuit diagram of a medical imaging system and a computer, FIGS. 2 and 3 show flow diagrams, FIGS. 4 to 8 show examples of possible scan paths, FIG. 10 shows a flow diagram, FIG. 11 shows examples of some scan points on a scan path and FIGS. 12 to 14 show flow diagrams.

DETAILED DESCRIPTION OF INVENTION

Figure 8:
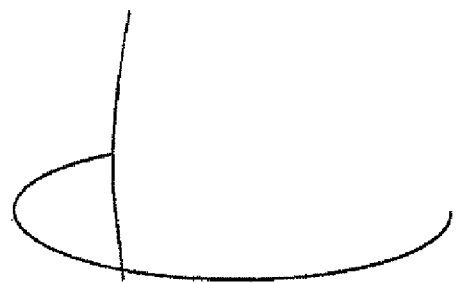

According to FIG. 1 a medical imaging system 1 has a radiation source 2 and a radiation detector 3. The radiation source 2 and radiation detector 3 are both movable. Generally—for example in C-arm x-ray systems—the radiation source 2 and radiation detector 3 are moved in such a manner that a connecting line 4 from the radiation source 2 to the radiation detector 3 always includes a central point 5 regardless of the current location of the radiation source 2 and radiation detector 3. A volume region 6 around the central point 5 corresponds to an examination region 6 of the medical imaging system 1.

In normal operation of the medical imaging system an examination object 7 (generally a person 7) is positioned in such a manner that a part of the examination object 7 to be examined (e.g. the brain or abdominal cavity of the person 7) is located as centrally as possible in the examination region 6. The procedure is then as follows, as set out in FIG. 2:

A user 8 of the medical imaging system 1 selects a recording program. A computer 9, which controls the medical imaging system 1, receives the selection of the user 8 in a step S1.

In a step S2 the computer 9 waits for a start command to be input. When the computer 9 receives the start command, in a step S3 the computer 9 starts to displace a recording arrangement 10 along a predetermined scan path. The recording arrangement 10 in particular comprises the radiation source 2 and radiation detector 3.

In a step S4 the computer 9 selects a first predetermined capture position.

In a step S5 the computer 9 checks whether the selected predetermined capture position has been reached. If so, in a step S6 the computer 9 captures a projection image P of the examination object 7 and stores it.

In a step S7 the computer checks 9 whether it has already captured and stored a projection image P for all the predetermined capture positions. If not, the computer 9 goes to a step S8, in which it selects the next predetermined capture position. It then goes back to step S5.

When the computer 9 has captured a projection image P for all the capture positions, in a step S9 it stops moving the recording arrangement 10 along the predetermined scan path.

The captured projection images P are generally analyzed by a computer other than the computer 9. In principle however the computer 9 could also carry out this processing operation. In the context of the present invention the essential steps for processing the projection images P as set out in FIG. 3 are as follows:

In a step S11 the computer 9 assigns the captured projection images P their corresponding projection matrices M.

In a step S12 the computer 9 uses a filtered back-projection algorithm to determine a three-dimensional reconstruction of the examination object 7 (or the relevant part of the examination object 7).

In a step S13 the computer 9 carries out further analyses of the three-dimensional reconstruction. Sectional representations or perspective views can be generated for example. Other analyses are also possible.

It can be seen from the above that the projection matrices M have to be known to the computer 9. Methods for determining the projection matrices M when the radiation source 2 is moved on a single circular scan path are known to those skilled in the art, for example from the technical paper [7]. However the scan path traveled in FIG. 2 is not circular. FIGS. 4 to 8 show examples of possible scan paths.

According to FIG. 4 a possible scan path has three segments. Each segment is circular per se. The segments adjoin each other orthogonally. They therefore describe the outer edges of an octant of a sphere.

Also according to FIG. 5 the scan path consists of a number of segments, with each segment in itself lying on a circular path. If the central point 5 is considered as the "earth's core" and the radiation source 2 is displaced on the "earth's surface", each segment extends from a "pole" common to the segments to the "equator". However they run on different "lines of longitude" from each other.

According to the example in FIG. 6 the scan path consists of two circles orthogonal to each other.

The configurations according to FIGS. 7 and 8 are also possible.

In all the examples in FIGS. 4 to 8 the segments of the scan path consist of circular paths or circle segments. But this is not mandatory. However with all the scan paths the region of the examination object 7 to be examined should be disposed close to the central point 5, for example in the vicinity of the "earth's core" in the example in FIG. 5.

The scan paths shown in FIGS. 4 to 8 correspond to the positions of the radiation source 2 in relation to the central point 5. The radiation detector 3 is diametrically opposite in each instance. A method for determining the projection matrices M for such scan paths, as described by way of example in conjunction with FIGS. 4 to 8, is the subject matter of the present invention.

To implement the inventive determination method, the computer 9 (or another computer) operates a computer program 11. The computer program 11 was created beforehand and stored in a mass storage device 12 of the computer 9 (e.g. a hard disk). For example the computer program 11 can be stored on a mobile data medium 13 and can be supplied to the computer 9 by means of the mobile data medium 13 by way of a suitable interface 14 of the computer 9. Examples of suitable data media are USB memory sticks, memory cards, CD-ROMs, etc. It is also possible to supply the computer program 11 to the computer 9 by way of a network interface 15.

The computer program 11 contains a sequence of machine commands, which can be executed by the computer 9. It causes the computer 9 to execute a determination method according to FIG. 10, when the computer program 11 is called by an operator of the computer 9 (it being possible for said operator to be identical to the user 8). Calling the computer program 11 causes the computer program 11 to be downloaded into the working memory of the computer 9 and be processed by the computer 9.

Figure 9:
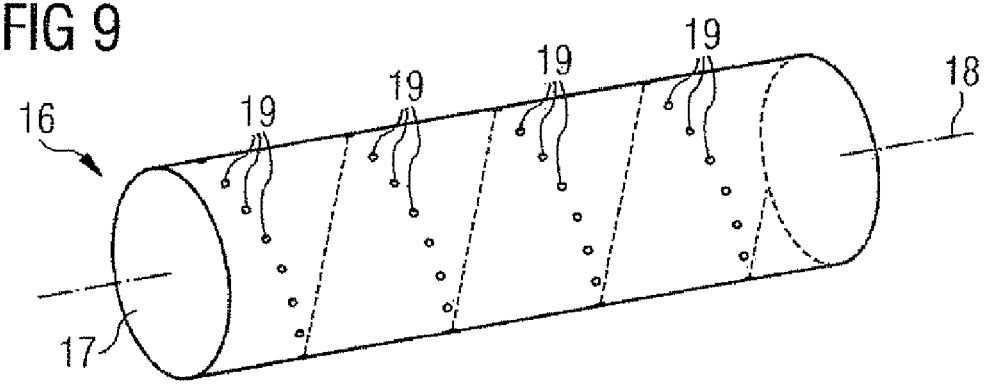
FIG. 9 shows a reference object.

In the context of the inventive determination method projection images are used which are projection images of a reference object 16. The reference object 16 can in principle be of any nature, as long as it allows determination of the projection matrices M. A standard reference object 16 is preferably used, for example a so-called PDS2 calibration phantom. Such a reference object 16 is shown in FIG. 9 and is described briefly below.

The PDS2 calibration phantom 16 has a cylindrical base body 17, which is transparent to radiation emitted by the radiation source 2; for example the base body 17 can be made of plastic.

Small spheres are disposed helicoidally around the edge of a central axis 18. The positions of the spheres 19 in the space are known in relation to a coordinate system, which is defined in relation to the PDS2 calibration phantom 16. Some of the spheres 19 have a large diameter (e.g. 3.2 mm), the others have a small diameter (e.g. 1.6 mm). The order of large and small spheres 19 is defined in such a manner that it can be determined from a sub-sequence of for example eight directly consecutive spheres 19, which sphere 19 is which in the sequence as a whole. The spheres 19 are also positioned in the base body 17 in such a manner that it is possible to determine the projection matrices from the projection images of the reference object 16. They are related to the above-mentioned coordinate system defined in relation to the reference object 16.

The determination of a projection matrix based on a projection image of the reference object 16 is known to and common practice for those skilled in the art. The applicant refers again to the above-mentioned technical paper [7].

The inventive determination method is described in more detail below in conjunction with FIG. 10. The descriptions relating to FIG. 10 also look more closely at acquisition of the projection images. Acquisition can be part of the inventive determination method but this is not absolutely necessary. It is only important that the necessary projection images of the reference object 16 are available.

According to FIG. 10 in a step S21 the reference object 16 is first disposed in a first location (position and orientation) in the examination region 6. The step S21 can be executed by the computer 9, in other words it triggers corresponding actuators, which position the reference object 16 accordingly. Alternatively positioning can be carried out by the user 8. The reference object 16 is preferably positioned in such a manner that its central axis 18 is approximately orthogonal to a circular path plane, which is defined by one of the segments of the scan path. Such positioning guarantees that the majority of the spheres 19 are visible in projection images still to be captured and that only a few of the spheres 19 overlap in these projection images. Identification of the spheres 19 is also relatively simple.

In a step S22 the computer 9 receives a first group G1 of first projection images P1 of the reference object 16. Step S22 corresponds in content to the acquisition described in conjunction with FIG. 2. Each projection image P1 of the first group G1 is therefore captured with corresponding positioning of the recording arrangement 10.

The projection images P1 of the first group G1 form a sequence of projection images P1. The sequence has sub-segments. Each sub-segment corresponds to the projection images P1, which were captured in a locally contiguous region of the scan path, in particular an individual circular path or circular path segment (see the above details relating to FIGS. 4 to 8).

In a step S23 the computer 9 checks whether it has already captured all the groups G1, G2, . . . of projection images P1, P2, . . . of the reference object 16. If not, the computer 9 goes to a step S24. In step S24 the reference object 16 is disposed in a further (second, third, . . . ) location in the examination region 6. Step S24 essentially corresponds (except for the new location) to step S21. The computer 9 then goes back to step S22.

If all the groups G1, G2, . . . of projection images P1, P2, . . . have already been captured, the computer 9 goes to a step S25. In step S25 the computer 9 selects those projection images P1, P2, . . . , based on which interim projection matrices M1, M2, are to be defined, from each group G1, G2, . . . . Alternatively the selection can be made automatically by the computer 9 or manually by the user 8.

In a step S26 (divided into two sub-steps S26a and S26b in FIG. 10 for the sake of clarity), the computer 9 checks whether at least one projection image P1, P2, . . . has been selected for each position of the recording arrangement 10. If not, the computer 9 goes back to step S25. Otherwise it goes to a step S27.

In step S27 (also divided into two sub-steps S27a and S27b in FIG. 10 for the sake of clarity) the computer 9 checks whether there is at least one position of the recording arrangement 10 for each group G2, G3, . . . —in other words except for the first group G1—for which a projection image P1, P2, . . . has been selected both in the respective group G2, G3, . . . and in at least one group G1, G2, . . . with a lower number. If not, the computer 9 goes back to step S25. Otherwise it continues the determination method with a step S28.

In step S28 the computer 9 uses the selected projection images P1, P2, . . . of the groups G1, G2, . . . to select interim projection matrices M1, M2, . . . in each instance. The interim projection matrices M1, M2, . . . in each instance describe a mapping of the three-dimensional space to a projection image P1, P2, . . . , which was captured with the respective positioning of the recording arrangement 10. Each determined interim projection matrix M1, M2, . . . is related to a coordinate system, which is defined by the respective location of the reference object 16. Within the groups G1, G2, . . . the interim projection matrices M1, M2, . . . are therefore related to the same coordinate system. However the coordinate systems differ from group G1, G2, . . . to group G1, G2, . . . . Each group G1, G2, . . . is therefore assigned a specific coordinate system.

Implementation of step S28 is possible for those skilled in the art without further ado. In the context of step S28 the positions of the spheres 19 are defined automatically or manually in each selected projection image P1, P2, . . . . The positions of the spheres 19 are then sorted, in other words placed in sequence—again automatically or manually. Next sub-sequences of spheres 19 are defined—again automatically or manually—which allow it to be concluded which sphere 19 is which—see also the above details relating to FIG. 9. The positions of the spheres 19 in space now known and the similarly known positions of the spheres 19 in the projection images P1, P2, . . . are then used—preferably independently by the computer 9—to define the interim projection matrices M1, M2, . . . . The interim projection matrices M1, M2, . . . contain all the geometric information necessary to describe the mapping of the three-dimensional space to the detector plan in full (or adequately).

The procedure in step S28 as such is known to those skilled in the art for individual projection matrices M1, M2, . . . . It can be adopted unchanged from the prior art, for example from the technical paper [7].

The projection matrices M1, M2, . . . are interim projection matrices. To determine the final projection matrices M the computer 9 can proceed as follows:

In a step S29 the computer 9 selects the second group G2 of projection images P2.

In a step S30 the computer 9 selects those positions of the recording arrangement 10, for which an interim projection matrix M1, M2, . . . has been determined, both in the currently selected group G2, G3, . . . of projection images P2, P3, . . . and also in a group G1, G2, . . . with a lower number.

In a step S31 the computer 9 uses the interim projection matrices M2, M3, . . . of the currently selected group G2, G3, . . . and the corresponding interim projection matrices M1, M2, . . . of the groups G1, G2, . . . with a lower number to determine a location of the coordinate system of the selected group G2, G3, . . . related to the coordinate system of the first group G1. The computer 9 preferably determines the location of the coordinate system using more than one—in particular every—such position of the recording arrangement 10. As a minimum the computer 9 uses a single such position of the recording arrangement 10.

If the computer 9 only defines the location of the coordinate system of the currently selected group G2, G3, . . . based on the interim projection matrices M1, M2, . . . of a single position of the recording arrangement 10, the relevant position of the recording arrangement 10 should be in the vicinity of but not precisely at the transition from one segment of the scan path to another segment of the scan path. This is described in more detail below in conjunction with FIG. 11.

Figure 11:
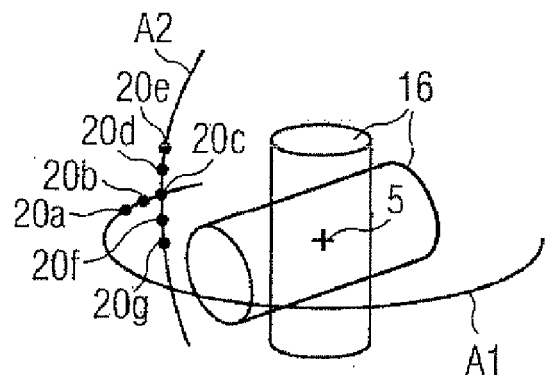

FIG. 11 shows a schematic diagram of the reference object 16 in a first location and a second location. FIG. 11 also shows two segments A1, A2 of the scan path. The two segments A1, A2 are—at least approximately—segments of a circle around the central point 5. The individual points 20a to 20g are intended to show positions of the radiation source 2, in which a projection image P1, P2, . . . is captured in each instance. Clearly the position 20c lies at the intersection of the two segments A1, A2. If the location of the coordinate system for the segment A2 is to be determined in relation to the location of the coordinate system for the segment A1 based on a single position of the recording arrangement 10, this determination is preferably carried out based on one of the positions 20a, 20b or 20d to 20g. The position 20c should however not be used for this.

In a step S32 (see FIG. 10 again) the computer 9 checks whether it has already carried out the steps S30 and S31 for all the groups G2, G3, . . . of projection images P2, P3, . . . . If not, in a step S33 the computer 9 selects the next group G3, G4, . . . of projection images P3, P4, . . . and goes back to step S30. Otherwise it continues the determination method with a step S34.

In step S34 the computer 9 uses the interim projection matrices M1, M2, . . . of the groups G1, G2, . . . and the locations of the coordinate system of the second, third, etc, groups G2, G3, . . . in relation to the coordinate system of the first group G1 for all positions of the recording arrangement 10 to define the final projection matrix M in each instance.

Definition takes place here in such a manner that all the final projection matrices M are related to a uniform coordinate system.

A possible refinement of step S34 in FIG. 10 is described in more detail below in conjunction with FIG. 12.

According to FIG. 12 in a step S41 the computer 9 selects the first group G1 of projection images P1.

In a step S42 the computer 9 selects the positions of the recording arrangement 10, for which first interim projection matrices M1 were determined based on the projection images P1 of the first group G1.

In a step S43 for the positions of the recording arrangement 10 selected in step S42 the computer 9 defines the first interim projection matrices M1 as final projection matrices M for these positions of the recording arrangement 10.

In a step S44 the computer 9 selects the next group G2, G3, . . . of projection images P2, P3, . . . .

In a step S45 the computer 9 selects those positions of the recording arrangement 10, for which an interim projection matrix M2, M3, . . . has been determined in the currently selected group G2, G3, . . . but for which no final projection matrix M has yet been defined.

For the positions of the recording arrangement 10 selected in step S45 in a step S46 the computer 9 defines the final projection matrices M based on the corresponding interim projection matrices M2, M3, . . . of the currently selected group G2, G3, . . . and the location of the coordinate system of the currently selected group G2, G3, . . . , in relation to the coordinate system of the first group G1.

In a step S47 the computer 9 checks whether steps S44 to S46 have already been executed for all groups G2, G3, . . . from the second group G2. If not, the computer 9 goes back to step S44. Otherwise the implementation of step S34 is completed.

The interim projection matrices M1, M2, . . . and also the final projection matrices M are preferably 3×4 matrices. For in this instance the projection matrices M, M1, M2, . . . can describe projective mappings. Projective mappings are generally known to and common practice for those skilled in the art. They are described for example in the technical publication [8]. Their important advantage is that they define a linear mapping in the homogeneous representation.

To implement step S46 in FIG. 12 it is possible to proceed as follows according to FIG. 13—for every individual position of the recording arrangement 10:

The following applies for the first interim projection matrix M1

$$x1 = M1X$$

X here is any point in the space, in relation to the coordinate system of the first group G1. x1 is the point in the plane, onto which the point X is mapped.

The following applies for the second interim projection matrix M2 determined for the same position of the recording arrangement 10

$$x2 = M2X$$

It is known that the interim projection matrices M1, M2, . . . can be converted to one another by means of a homographic transformation matrix M', so the following applies $$x1 = M2M'X$$

In a step S51 the computer 9 therefore defines a homographic transformation matrix M'. The homographic transformation matrix M' is a 4×4 matrix, by means of which the three-dimensional space of the coordinate system of the group G2, G3, selected in step S44 is transformed to the coordinate system of the first group G1.

The homographic transformation matrix M' has 4×4=16 matrix coefficients. In a step S52 the computer 9 therefore defines at least eight 2D-3D correspondence pairs of points (spheres 19) in corresponding projection images P2, P3, . . . and P1 of the currently selected group G2, G3, . . . and of the first group G1. Each correspondence pair supplies two equations with linear independence. This results in an equation system, in which 16 unknowns, namely the 16 matrix coefficients of the homographic transformation matrix M', occur. This equation system can be resolved. The path to resolution is described for example in the technical publication [8]. It is therefore possible for the computer 9 to determine the matrix coefficients of the homographic transformation matrix M' in a step S53, thereby determining a transformation specification, based on which the interim projection matrices M2, M3, . . . of the currently selected group G2, G3, . . . can be transformed to the coordinate system of the first group G1.

The step S53 in FIG. 13 can be implemented in different possible ways. The computer 9 preferably carries out a singular value decomposition of the linear equation system, based on which the matrix coefficients of the homographic transformation matrix M' can be determined. Based on the singular value decomposition it then determines the matrix coefficients of the homographic transformation matrix M'.

The procedure in FIG. 13 is only exact in theory. In practice inevitable inaccuracies (e.g. the limited resolution of the radiation detector 3) cause errors to occur. Therefore deviations—which may only be minor—result between the measured "true" position of the spheres 19 and the positions of the spheres 19 calculated after the coordinate transformation for example in the projection images P2, P3, . . . of the selected group G2, G3, . . . in relation to the other pixels, which were not used to define the matrix coefficients. It is therefore possible to implement step S52 in such a manner that not only eight but more than eight—in particular significantly more than eight—2D/3D correspondence pairs can be selected. The corresponding procedure is also known from the technical publication [8]. The predetermined 2D/3D correspondence pairs can alternatively be taken from a single pair of corresponding projection images P2, P3, . . . and P1 or a number of pairs of such projection images P1, P2, . . . .

If more than eight 2D/3D correspondence pairs are predefined for the computer 9, the computer 9 optimizes a two-dimensional degree of error for the positions of the spheres 19 in the relevant projection images P2, P3, . . . in relation to the projection images P2, P3, . . . . Generally it is sufficient to analyze approximately 20 to 30 pixels.

The procedure described above in conjunction with FIG. 12 is possible but not optimal. It is currently preferable to modify the procedure in FIG. 12 as described in more detail below in conjunction with FIG. 14.

According to FIG. 14 the steps S42 and S45 in FIG. 12 are replaced by steps S61 and S62. The other steps (steps S41, S43, S44, S46 and S47) are retained.

In step S61—as in step S42—those positions of the recording arrangement 10 are also selected, for which an interim projection matrix M1 was determined in the first group G1. In contrast to step S42 however only complete sub-segments of the sequence (or locally contiguous segments of the scan path) are selected. Step S61 can alternatively be executed independently by the computer 9 or by the user 8.

In a similar manner only complete sub-segments of the respectively selected second, third, . . . group G2, G3, . . . , for which corresponding interim projection matrices M2, M3, . . . were determined, are also selected in step S62. It is insignificant in the context of step S62 whether interim projection matrices M1, M2, ... with a low number were determined in the selected sub-segments.

Modifications are of course also possible. Thus in particular when the selections in steps S42 and S61 on the one hand and S45 and S62 on the other hand are made manually, it may also be permitted for the user 8 to select interim projection matrices M1, M2, ..., which only correspond respectively to parts of circular paths or circular path segments.

The present invention can in particular be used with C-arm x-ray systems. It is simple to implement, numerically stable and can be added on to these without any modification to the calibration method known per se. It is particularly advantageous, if individual segments of the scan path lie respectively in a planar plane, for example forming a circle or a circle segment.

The above description serves exclusively to explain the present invention. The scope of protection of the present invention should in contrast only be defined by the attached claims.

REFERENCES

[1] L. A. Feldkamp, L. C. Davis, J. W. Kress: Practical Cone-Beam Algorithm, J. Opt. Soc. Am. A, vol. 1, no. 6, pages 612-619, June 1984
[2] A. Katsevich: Image Reconstruction for the Circle and Arc Trajectory, Physics in Medicine and Biology, vol. 50, no. 10, pages 2249-2265. April 2005
[3] J. Pack, F. Noo: Cone-Beam Reconstruction Using 1D Filtering Along the Projection of M-Lines, Inverse Problems, vol. 21, no. 3, pages 1105-1120, April 2005
[4] H. Kudo, T. Saito: Fast and Stable Cone-Beam Filtered Backprojection Method for Non-Planar Orbits, Physics in Medicine and Biology, vol. 43, no. 4, pages 747-760, 1998
[5] X. Wang, R. Ning: A Cone Beam Reconstruction Algorithm for Circle-plus-Arc Data-Acquisition Geometry, IEEE Transactions on Medical Imaging, vol. 18, no. 9, pages 815-824, 1999
[6] X. Tang, R. Ning: A Cone Beam Filtered Backprojection (CB-FBP) Reconstruction Algorithm for a Circle-plus-two-Arc Orbit, Medical Physics, vol. 28, no. 6, pages 1042-1055,
[7] N. Strobel, B. Heigl, T. Brunner, O. Schütz, M. Mitschke, K. Wiesent, T. Mertelmeier: Improving 3D Image Quality of X-Ray C-Arm Imaging Systems by Using Properly Designed Pose Determination Systems for Calibrating the Projection Geometry, Medical Imaging 2003: Physics of Medical Imaging. Edited by Yaffe, Martin J.; Antonuk, Larry E. Proceedings of the SPIE, vol. 5030, pages 943-954, 2003
[8] R Hartley, A. Zisserman: Multiple View Geometry in Computer Vision, Cambridge University Press, Cambridge UK, Second Edition 2003

The invention claimed is:

1. A method for determining final projection matrices, comprising:
   capturing a plurality of projection images via a recording arrangement with corresponding positioning of the recording arrangement;
   receiving by a computer a plurality of groups of projection images of a reference object already known to the computer;
   determining an interim projection matrix via one of the plurality of projection images for the respective position of the recording arrangement, where the interim projection matrix describes a mapping of the three-dimensional space to a projection image captured with respective positioning of the recording arrangement and being related to a coordinate system;
   assigning a specific coordinate system to each groups of projection images;
   determining locations of the other coordinate systems related to one of the coordinate systems by the computer using interim projection matrices of different groups determined for the same position of the recording arrangement; and
   defining the final projection matrix by the computer using the interim projection matrices and the locations of other coordinate systems for each position of the recording arrangement, wherein the final projection matrices relate to a uniform coordinate system.

2. The method as claimed in claim 1, wherein the interim projection matrices and the final projection matrices are 3×4 matrices, that define a projective mapping.

3. The method as claimed in claim 2, wherein the computer adopts the interim projection matrix for at least one position of the recording arrangement, for which it has determined an interim projection matrix related to the one coordinate system, as the final projection matrix and determines the final projection matrix for at least one position of the recording arrangement, for which it has determined an interim projection matrix related to another coordinate system, based on the respective interim projection matrix related to the other coordinate system and the location of the other coordinate system.

4. The method as claimed in claim 3, wherein the final projection matrices form a sequence having sub-segments, the final projection matrices of each sub-segment correspond to a locally contiguous segment of a scan path, along which the recording arrangement is displaced and the computer determines the final projection matrices based on the interim projection matrices of the same group within each sub-segment.

5. The method as claimed in claim 4, wherein the computer determines a homographic transformation matrix for every other coordinate system, by means of which the three-dimensional space of the respective other coordinate system is transformed to the one coordinate system and the computer uses the respective homographic transformation matrix to transform the interim projection matrices related to the respective other coordinate system to the one coordinate system.

6. The method as claimed in claim 5, wherein the computer determines the homographic transformation matrices by resolving linear equation systems.

7. The method as claimed in claim 6, wherein the computer carries out a singular value decomposition to resolve the linear equation systems.

8. A non-transitory computer readable medium storing a computer program for execution by a computer comprising:
   receiving by the computer a plurality of groups of projection images of a reference object already known to the computer,
   determining an interim projection matrix via one of a plurality of captured projection images for the respective position of the recording arrangement, where the interim projection matrix describes a mapping of the three-dimensional space to a projection image captured with respective positioning of the recording arrangement and being related to a coordinate system, wherein the captured projection images are captured via a recording arrangement;
   assigning a specific coordinate system to each group of projection images; determining locations of the other coordinate systems related to one of the coordinate systems by the computer using interim projection matrices of different groups determined for the same position of the recording arrangement; and defining the final projection matrix by the computer using the interim projection matrices and the locations of other coordinate systems for each position of the recording arrangement, wherein the final projection matrices relate to a uniform coordinate system.

9. The non-transitory computer readable medium as claimed in claim 8, wherein the interim projection matrices and the final projection matrices are 3×4 matrices, that define a projective mapping.

10. The non-transitory computer readable medium as claimed in claim 9, wherein the computer adopts the interim projection matrix for at least one position of the recording arrangement, for which it has determined an interim projection matrix related to the one coordinate system, as the final projection matrix and determines the final projection matrix for at least one position of the recording arrangement, for which it has determined an interim projection matrix related to another coordinate system, based on the respective interim projection matrix related to the other coordinate system and the location of the other coordinate system.

11. The non-transitory computer readable medium as claimed in claim 10, wherein the final projection matrices form a sequence having sub-segments, the final projection matrices of each sub-segment co/respond to a locally contiguous segment of a scan path, along which the recording arrangement is displaced and the computer determines the final projection matrices based on the interim projection matrices of the same group within each sub-segment.

12. The non-transitory computer readable medium as claimed in claim 11, wherein the computer determines a homographic transformation matrix for every other coordinate system, by means of which the three-dimensional space of the respective other coordinate system is transformed to the one coordinate system and the computer uses the respective homographic transformation matrix to transform the interim projection matrices related to the respective other coordinate system to the one coordinate system.

13. The non-transitory computer readable medium as claimed in claim 12, wherein the computer determines the homographic transformation matrices by resolving linear equation systems.

14. The non-transitory computer readable medium as claimed in claim 13, wherein the computer carries out a singular value decomposition to resolve the linear equation systems.

15. A computer, comprising:
a processor;
an input device;
and output device; and
a mass storage device having a stored program that:
receives a plurality of groups of projection images of a reference object already known to the computer;
determines an interim projection matrix via one of a plurality of captured projection images for the respective position of the recording arrangement, where the interim projection matrix describes a mapping of the three-dimensional space to a projection image captured with respective positioning of the recording arrangement and being related to a coordinate system, wherein the captured projection images are captured via a recording arrangement;
assigns a specific coordinate system to each group of projection images;
determines locations of the other coordinate systems related to one of the coordinate systems by the computer using interim projection matrices of different groups determined for the same position of the recording arrangement; and
defines the final projection matrix by the computer using the interim projection matrices and the locations of other coordinate systems for each position of the recording arrangement, wherein the final projection matrices relate to a uniform coordinate system.

16. The computer as claimed in claim 15, wherein the interim projection matrices and the final projection matrices are 3×4 matrices, that define a projective mapping.

17. The computer as claimed in claim 16, wherein the computer adopts the interim projection matrix for at least one position of the recording arrangement, for which it has determined an interim projection matrix related to the one coordinate system, as the final projection matrix and determines the final projection matrix for at least one position of the recording arrangement, for which it has determined an interim projection matrix related to another coordinate system, based on the respective interim projection matrix related to the other coordinate system and the location of the other coordinate system.

18. The computer as claimed in claim 17, wherein the final projection matrices form a sequence having sub-segments, the final projection matrices of each sub-segment correspond to a locally contiguous segment of a scan path, along which the recording arrangement is displaced and the computer determines the final projection matrices based on the interim projection matrices of the same group within each sub-segment.

19. The computer as claimed in claim 18, wherein the computer determines a homographic transformation matrix for every other coordinate system, by means of which the three-dimensional space of the respective other coordinate system is transformed to the one coordinate system and the computer uses the respective homographic transformation matrix to transform the interim projection matrices related to the respective other coordinate system to the one coordinate system.

20. The computer as claimed in claim 19, wherein the computer determines the homographic transformation matrices by resolving linear equation systems.

* * * * *